US010874880B2

(12) United States Patent
Ovejero Mayoral (10) Patent No.: US 10,874,880 B2
(45) Date of Patent: Dec. 29, 2020

(54) METHOD FOR THE AUTOMATION OF THE DOSE CALIBRATION, RECONSTRUCTION AND VERIFICATION OF COMPLEX RADIOTHERAPY TREATMENTS, INTEGRATED INTO ONE ENVIRONMENT, AND SYSTEM FOR IMPLEMENTING SAME

(71) Applicant: Maria Del Carmen Ovejero Mayoral, Seville (ES)

(72) Inventor: Maria Del Carmen Ovejero Mayoral, Seville (ES)

(*) Notice: Subject to any disclaimer, the term of this patent is extended or adjusted under 35 U.S.C. 154(b) by 20 days.

(21) Appl. No.: 16/324,279

(22) PCT Filed: Aug. 10, 2017

(86) PCT No.: PCT/ES2017/070577
§ 371 (c)(1),
(2) Date: Feb. 8, 2019

(87) PCT Pub. No.: WO2018/029392
PCT Pub. Date: Feb. 15, 2018

(65) Prior Publication Data
US 2019/0192882 A1 Jun. 27, 2019

(30) Foreign Application Priority Data
Aug. 10, 2016 (ES) .................. 201631090

(51) Int. Cl.
*A61N 5/10* (2006.01)
*A61B 6/00* (2006.01)
*G16H 20/40* (2018.01)

(52) U.S. Cl.
CPC ............. *A61N 5/1077* (2013.01); *A61B 6/00* (2013.01); *A61N 5/10* (2013.01); *A61N 5/1048* (2013.01);
(Continued)

(58) Field of Classification Search
None
See application file for complete search history.

(56) References Cited

U.S. PATENT DOCUMENTS 6,675,116 B1  1/2004  Ritt
8,160,204 B2  4/2012  Muller et al.
(Continued)

FOREIGN PATENT DOCUMENTS

EP  2050395 A1  4/2009
ES  2309093 T3  12/2008
(Continued)

OTHER PUBLICATIONS

Wong et al., "A silicon strip detector does magnifying glass for IMRT dosimetry," Med. Phys., Jan. 6, 2010, pp. 427-439, vol. 37, No. 2.
(Continued)

*Primary Examiner* — Hoon K Song
(74) *Attorney, Agent, or Firm* — Im IP Law; Chai Im; C. Andrew Im (57) ABSTRACT

A method for automation and integration inside a same setting of the characterization of a beam accelerator and the verification of a radiotherapy treatment based on the use of a detection medium and its control in a remote way. The reading of the detector subsystem placed on the flat mannequin is calibrated and dosimetric response of the detector subsystem is obtained in automated matter. 3D reconstruction of the radiotherapy treatment is applied on the detector subsystem based on measurements taken with the detector subsystem in the axial plane. Verification and automated visualization of a dose map reconstructed from the measurements taken with the detector subsystem with the dose map is obtained with a planning system.

11 Claims, 7 Drawing Sheets (52) U.S. Cl.
CPC .............. *A61N 5/1071* (2013.01); *A61B 6/42* (2013.01); *A61N 5/1001* (2013.01); *A61N 2005/1074* (2013.01); *A61N 2005/1076* (2013.01); *A61N 2005/1092* (2013.01); *G16H 20/40* (2018.01)

(56) References Cited

U.S. PATENT DOCUMENTS

| | | | | |
|---|---|---|---|---|
| 2015/0283403 | A1* | 10/2015 | Kapatoes | A61N 5/1071 600/1 |
| 2015/0316657 | A1* | 11/2015 | Ruschin | G01T 1/08 250/252.1 |
| 2017/0312547 | A1* | 11/2017 | Wong | A61N 5/1075 |

FOREIGN PATENT DOCUMENTS

| | | | |
|---|---|---|---|
| ES | 2303403 | B1 | 5/2009 |
| ES | 2409760 | B1 | 3/2014 |
| ES | 2453944 | T3 | 4/2014 |
| KR | 20130059668 | A | 6/2013 |
| WO | 01/60236 | A2 | 8/2001 |

OTHER PUBLICATIONS

Lee et al., Retrospective IMRT Dose Reconstruction Based on Cone-Beam CT and MLC Log-File, Int. J. Radiation Oncology Biol. Phys., Jan. 14, 2008, pp. 634-644, vol. 70, No. 2.

Nicolini et al., GLAaS: An absolute dose calibration algorithm for an amorphous silicon portal imager. Applications IMRT verifications, Med. Phys., Jul. 21, 2006, pp. 2839-2851, vol. 33, No. 8.

Eckhause et al., Automating linear accelerator quality assurance, Med. Phys., Oct. 2015, pp. 6074-6083, vol. 42, No. 10.

Defoor et al., "Anatomy-based, patient-specific VMAT QA using EPID or MLC log files," J. Appl. Clin. Med. Phys., May 8, 2015, pp. 206-215, vol. 16, No. 3.

* cited by examiner

METHOD FOR THE AUTOMATION OF THE DOSE CALIBRATION, RECONSTRUCTION AND VERIFICATION OF COMPLEX RADIOTHERAPY TREATMENTS, INTEGRATED INTO ONE ENVIRONMENT, AND SYSTEM FOR IMPLEMENTING SAME

RELATED APPLICATIONS

This application is a § 371 application of PCT/ES2017/070577 filed Aug. 10, 2017, which claims priority from Spanish Patent Application No. 201631090 filed Aug. 10, 2016, each of which is incorporated herein by reference in its entirety.

FIELD OF THE INVENTION

The invention relates to fields of medical physics and biomedicine. More particularly, the invention relates to a method for an automated dosimetric calibration, reconstruction and verification of complex radiotherapy treatments integrated in a setting based on silicon monolithic detectors technology. The invention affects equally either the system or the installation of its implementation.

BACKGROUND OF THE INVENTION

In order to guarantee the quality in radiotherapy treatments, there are multiple recommendations coming from different institutions that show how to carry out the quality control of the accelerators used in radiotherapy: "International Electrotechnical Commission" (IEC 977), "Institute of Physics and Engineering in Medicine" (IPEM 81), "American Association of Physicists in Medicine" (AAPMTG40).

Such recommendations state the parameters that need to be measured as well as the regularity to revise them. Those revisions have traditionally been carried out with a dosimeter in a water phantom: the dosimeter moves to the three different directions of the water phantom in order to take accurate measurements of the dose in different water depths, following the recommendations and protocols from different institutions. Furthermore, there are several commercialized systems as Multicube, produced by Iba Dosimetry, which allows determining the characteristics of an accelerator beam from dose measurements with ionization chambers without using the water phantom.

There are also new developments like the one found in the article "Automating linear accelerator quality assurance" by Eckhause T[1], Al-Hallaq H[2], Ritter T[3], Med. Phys. October 2015. The evaluation of the performance is also shown in this article, using the system log files and the Electronic Portal Imaging Devices or EPID.

On the other hand, multiple systems and methods to verify treatments before being administered to a patient have been developed. The techniques, which are progressively more complex in radiotherapy treatments (as VMAT), also need procedures to assure the quality that allow verifying them with a high level of precision and consistency. To determine the absorbed dose in external beam radiotherapy, the International Atomic Energy Agency (IAEA) and the International Commission on Radiation Units and Measurements (ICRU) have created several reports and codes of practice. Among them, we find the ICRU report no 24 ("Determination of Absorbed Dose in a Patient Irradiated by Beams of X or Gamma Rays in Radiotherapy Procedures"), where the need to supply an absorbed dose with a 5% standard precision is mentioned. This is a widely discussed limit; in fact, there have been suggestions of a 2% limit since 1976 in the relative dose measurement for low-grading profiles. As regards the spatial resolution in the dose measurement, there is equally no uniformity criterion, being 2 mm the most exacting criterion in areas with high dose gradients.

Following these recommendations there are several commercialized systems as well as new developments carried out by different research institutions that verify a treatment before administering it to a patient. The verification methods and systems of radiotherapy treatments that exist nowadays can be classified into: detectors, EPID, software systems based on linear accelerator logs and traditional systems based on radiographic or radiochromic film.

Among the commercialized systems we find 2D detection systems based on ionization chambers and silicon diodes. The systems MapCHECK and MapCHECK2, which are manufactured by Sun Nuclear, are based on n-type diode, whereas I'MRT MatriXX created by IBA dosimetry group and OCTAVIUS 729 (PTW Freiburg GmbbH) are based on ionization chambers. Apart from the detector technology, these systems differ in the arrangement and distance between them. The spatial resolution of these systems depends on the distance between the detection elements. They allow obtaining dose maps through interpolation algorithms. The commercialized systems based on 2D arrays not only allow the checking of each field but also a real-time treatment verification.

The Electronic Portal Imaging Device is another commercial option related to the accelerator which allows us to measure its exit fluence as well as the position of the Multileaf Collimator. Many systems have been developed based on several technologies. The spatial resolution is better than the one of 2D array detectors but the instrument calibration is more complex. There are references like the article "Anatomy-based, patient-specific VMAT QA using EPID or MLC log files" by Defoor DL[1], Vazquez-Quino LA, Mavroidis P, Papanikolaou N, in J Appl Clin Med Phys. 2015 May 8 where it starts being discussed the use of a system and method that allows verifying a complex treatment based on the use of EPID and the log files of an accelerator.

All these systems have the advantage of providing a real-time dose if compared to traditional methods based on radiographic or radiochromic film detection. However, their spatial resolution concerning the centimeters is worse. They need a complex electronics system due to the big amount of channels and they are not effective in order to obtain dose maps in axial levels that fulfill the ICRU requirements.

Aiming to solve the problems that 2D commercial systems present, other systems based on segmented semiconductor detectors started to be developed: this type of detector is widely used in medical imaging (like PET) and in high-energy physics.

In order to improve the spatial resolution, within the European project frame MAESTRO (Methods and Advanced Equipment for Simulation and Treatment in Radio Oncology) a monolithic detector has been developed which was used to measure dose maps comparing its results to the MapCHECK system; the results were positive.

A silicon pixel array has also been developed in DOSI, whose characteristics have been carried out in comparison to ionization chambers and diamond detectors, showing a good concordance. Any of these two systems is suitable to measure dose maps in the axial level, since the associated reading system is too ample. The RADIA collaboration presents the patent no ES2409760, whose main innovation is the first prototype of a system that allows measuring doses in the axial level with a silicon monolithic detector. Its spatial resolution is better than those from current commercialized systems. However, it does not solve the problem of obtaining and verifying the dose map in real time.

This way, we find the patent document no ES 2 453 944 ("Method and device for IMRT verification") which shows a method and a system that verify a real time 3D IMRT treatment from measures taken to the accelerator beam from a perpendicular level. Such method does not take into account the information coming from the accelerator logs.

The document no ES 2 303 403 ("Method and system for the validation of an external radiotherapy treatment") focuses on correcting Multileaf Collimator errors from direct measurements without using the files of the accelerator log.

The patent no ES 2 309 093 T3 ("Automated calibration for radiation dosimetry") is about procedures to automate dose calibration through radiographic films, without obtaining a real time response.

There are other systems and methods; some patent documents are mentioned as for example:

The Korean patent application document KR20130059668 ("Multidimensional phantom for quality assurance of intensity modulated radiation therapy and stereotactic body radiation therapy") allows measuring the dose distribution in a dimension with an ionization chamber but it does not allow either the reconstruction or the verification of a dose map.

In the Spanish patent no ES2409760 ("System and method of verification of radiotherapy treatments") the reconstruction of a dose map in the axial plane is by contrast allowed, using an algorithm based on the measurements taken with a segmented silicon strip detector, but only in a plane. Neither does it include a procedure to allow its obtaining in real time nor the verification of the reconstructed treatment comparing it to another one calculated with a planning system, nor a previous procedure that allows characterizing the accelerator beam and contrasting it with the accelerator log files.

In addition, the European patent EP2050395 ("Methods for improving image quality of image detectors, and systems therefor") presents a method to improve the quality of the image through the offset subtraction in silicon detectors used in radiotherapy. However, this method does not allow either to rebuild or to verify the radiotherapy treatment.

Consequently, nowadays there is not any solution that allows the characterization of the accelerator beam and the verification of a radiotherapy treatment, evaluating the concordance between the calculation of a planning system or TPS and the dose distribution supplied by the accelerator. This verification is made not only through a direct measurement with an axial plane system, but also with the research of possible deviations that result in the accelerator logs and the integration of the planner in the same setting at the same time.

SUMMARY AND OBJECT OF THE INVENTION

The aim of this invention is to solve the state of the art integrating in the same setting the characterization of an accelerator beam and the verification of a radiotherapy treatment, having an effect not only in the clinical presentation but also in the organization of the work, reducing the time needed for each patient.

In a practical implementation of the invention, the system and method allow verifying a radiotherapy treatment evaluating the concordance between the TPS calculation and the dose distribution provided by the accelerator. The agreement between the planned dose and the measurement is obtained using different parameters, as non-limiting example, 2D gamma, 3D gamma and dose-volume histograms. The system and method allow the distribution of dose provided by the accelerator to be evaluated by the direct measurement when coming out of the axial plane or with the study of the possible deviations leading from the analysis and the processed information from the accelerator logs. The system and method also allow integrating in the same system or setting the result of the planned dose calculation through a TPS (which could be based on Monte Carlo calculation).

To this end, and in a more precise way, the invention is about a method that allows automating the remote control of the medium for the acquisition of the system signal, calibrating a dose response pattern in reference conditions, and also obtaining in an automated way the parameters that allow the characterization of an accelerator beam (non-limiting example: isodose distribution, cross section profiles, output depth and output factor.)

The system and method also allow in an automated way:
  Making the characterization of the accelerator beam in reference and non-reference conditions for the different combinations of energy, field size and source-surface distance used in radiotherapy treatments.
  Reconstructing and visualizing in 3D a radiotherapy treatment from direct measurements of the axial plane with uncertainty values lower than 1% and a spatial resolution better than 2 mm or from an accelerator information logs or files.
  Verifying and visualizing the parameters that allow such verification in a radiotherapy treatment thanks to a system composed by a segmented semiconductor detector, an acquisition system and a user interface that will be described below.

In order to carry out this method is necessary to have a system where a detectors subsystem takes part. This segmented detectors subsystem with a guard ring is located in parallel planes with a minimum distance of 3 mm between them. The space between them is carried out with a material layer that permits to maintain the electronic balance conditions.

Such subsystem based on monolithic detectors needs for its operation to be polarized inversely. The detector output in these conditions is not only due to the dose accumulation that we want to verify but there is also a factor whose origin comes from the own dark current detector. This factor must be checked to reduce the uncertainties present in the dose map that has been obtained. The methodology described here can be applied to a different detector type not only to segmented silicon detectors.

Similarly, some mannequins take part in the system by placing the detector subsystem in the required conditions to carry out the dosimetry.

Precisely, a flat mannequin that allows the characterization of the accelerator beam in reference conditions, as well as out of them, and a cylindrical mannequin to verify a radiotherapy treatment.

The detector subsystem is complemented with a control and data acquisition system which has a number of channels that allow reading every strip or pixel from the detector subsystem.

The control subsystem allows rotating the cylindrical mannequin using an engine, thus controlling its angular position instantaneously thanks to the use of an angle sensor subsystem. This subsystem can rotate at the same angular velocity than the gantry accelerator, at the same time the accelerator delivers a complex treatment, as VMAT.

The detector signal is digitized by the data acquisition system. Such acquisition system allows the digitization using a digital analog converter whose number of bits and sample of frequency allow minimizing the uncertainty of the dose measurement.

The digitized information is arranged in the acquisition system, together with the information whose origin is in the accelerator, following a communications protocol, as non-limiting example of the execution, Ethernet. Such information may be sent and stored in a PC or process and storage system through a communications bus, which may also allow integrating the data coming from the planning system. The human machine interface (hereinafter HMI) allows not only the configuration and management of the control and data acquisition system but also the access and visualization of beam characterization parameters, measurements, reconstruction and verification of the treatment.

The radiotherapy treatment 3D reconstruction based on the measurements taken by the detector subsystem is obtained using as the basis 2D reconstructed images.

The verification or evaluation of such parameters will allow validating or checking possible errors. In other words, if they do not meet the established criteria in advance, the system and method will allow repeating the process until a logout whose parameters meet such criteria is obtained.

This way we get a method and system that integrate in an only platform the mediums to optimize the workflow and the clinical results.

DESCRIPTION OF THE DRAWINGS

In order to complement the next description and to get a better understanding of the invention characteristics, according to a preferential example of a practical implementation, this description goes with a set of drawings where with an illustrative and non-limiting character the following is represented.

PREFERRED EMBODIMENTS OF THE INVENTION

In a practical implementation of the invention of the method and system to integrate in the same platform the characterization of a beam accelerator and the verification of a radiotherapy treatment, evaluating the concordance between the TPS calculation and the dose distribution provided by the accelerator, the method and system allow the dose distribution provided by the accelerator in a radiotherapy treatment to be evaluated by the direct measurement in the axial plane and the study of possible deviations, analysis and processed information coming from the accelerator logs. The method and system allow integrating in the same range the planned dose calculation by a TPS and the provided dose. The agreement between the planned dose and the provided one by the accelerator is obtained by using different parameters, being non-limiting examples of the implementation, the 2D gamma, the 3D gamma and Dose-Volume Histograms (DVH), Tumour Control Probability (TCP), Normal Tissue Complication Probability (NTCP).

Figure 2:
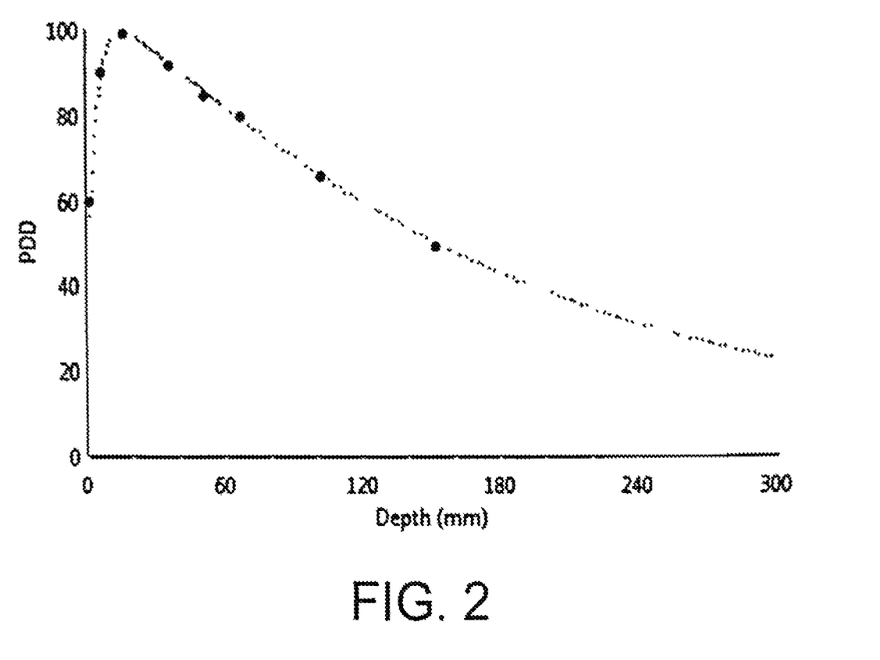
FIG. 2 illustrates the analysis for the calculation of the depth dose performance within the mediums for the user.
Figure 4:
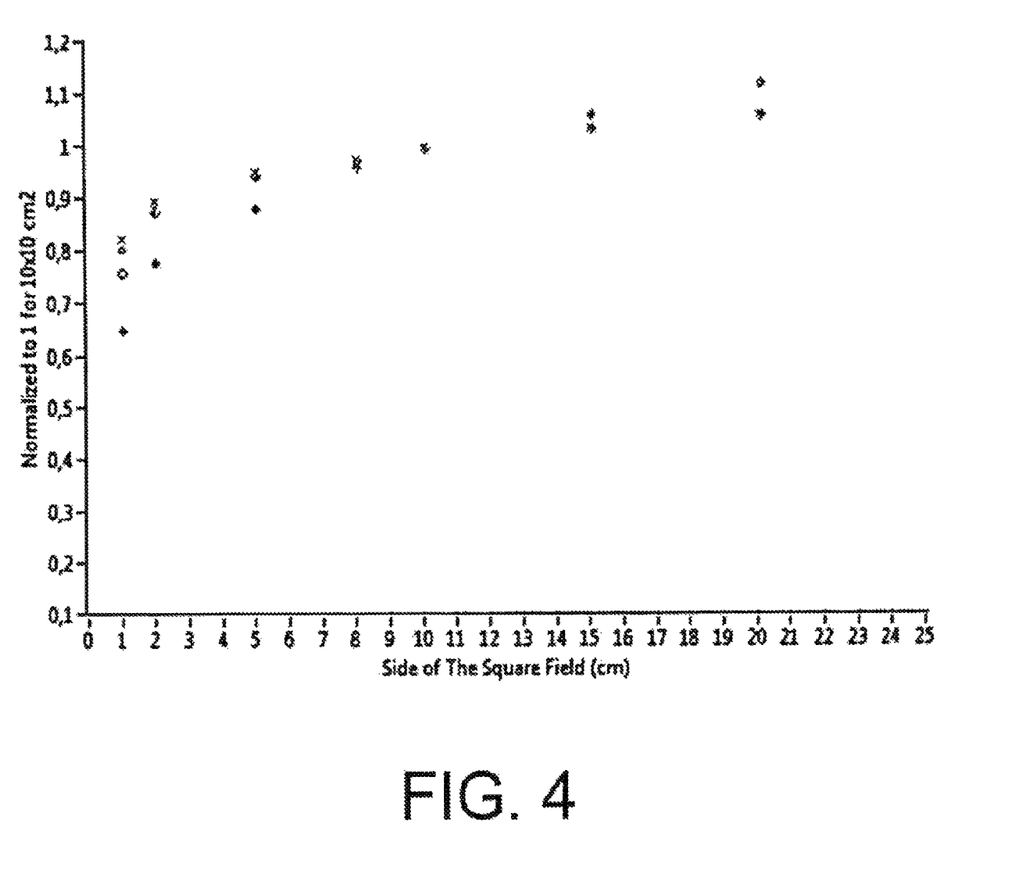
FIG. 4 shows how the calculation of the output factor is visualized.
Figure 5:
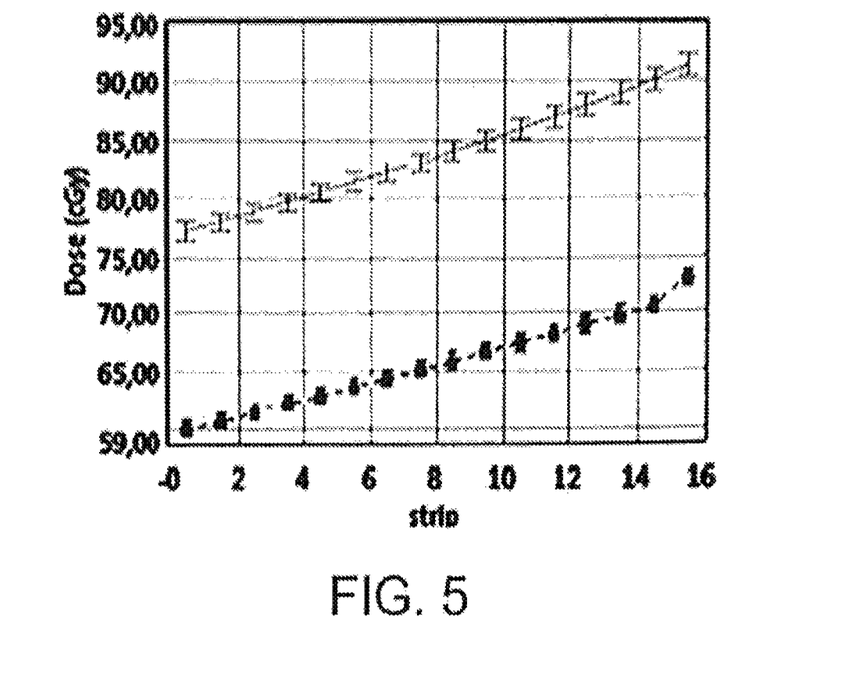
FIG. 5 illustrates the characterization in the axial plane for a segmented strip detector.
Figure 6:
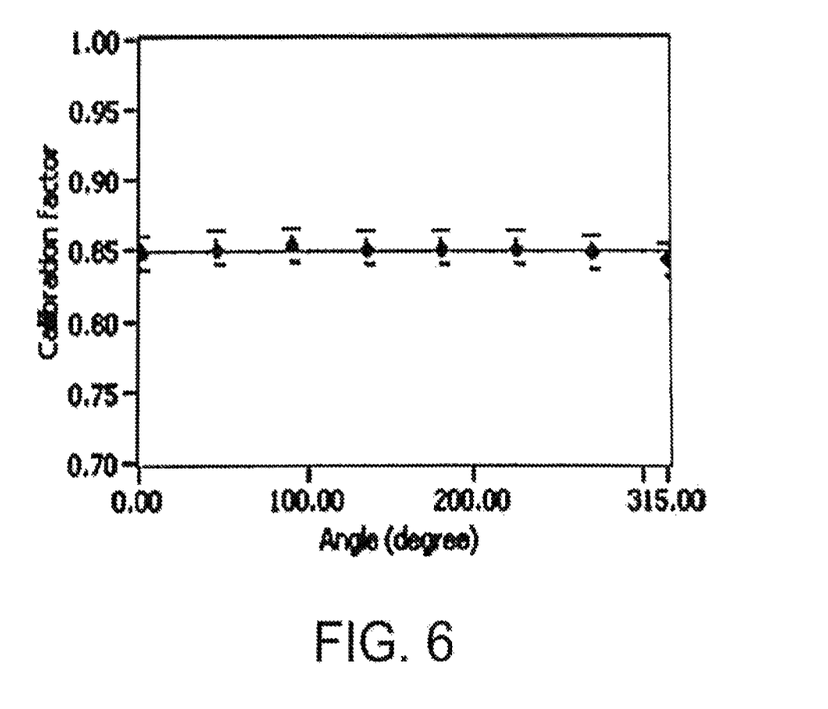
FIG. 6 illustrates the procedure to calculate the calibration factor for a segmented strip detector using different angles of incidence.
Figure 8:
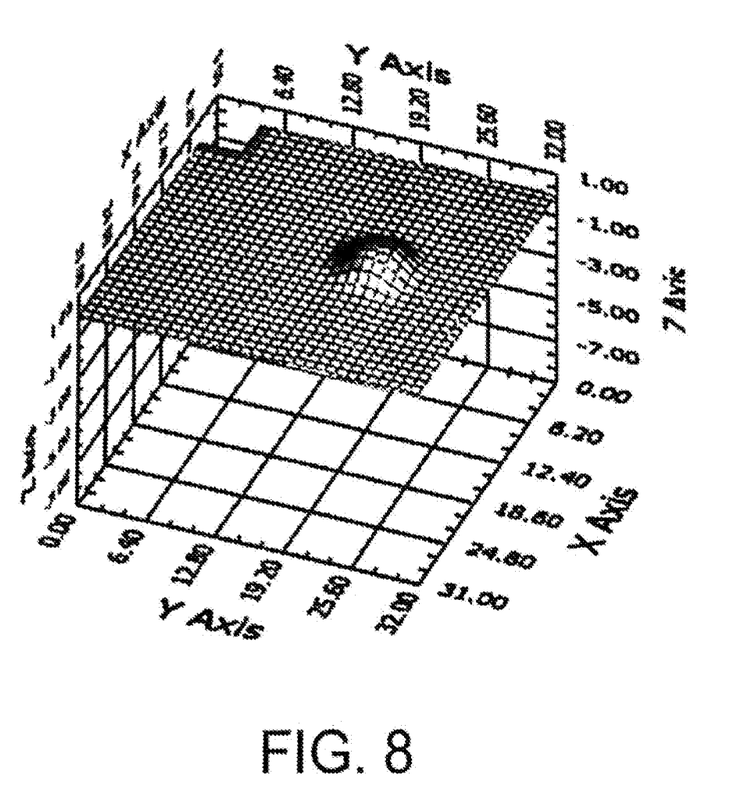
FIG. 8 shows an example of the algorithm application for the reconstruction of the dose map for a 32-strip detector, for a circular dose distribution (whose circle is not in the middle) with radius 3a (where a is the strip width)

In a more precise way, as shown in FIGS. 10-13, it is defined the system (2) to integrate the characterization of a beam of the accelerator (21) and the verification of a 3D radiotherapy treatment (22) based not only on measurements obtained in the same exit plane of such radiation beam, but also in the information included in the accelerator files. This system comprises the following stages:

a. Configuration, control, monitoring and automation of reading systems after irradiating with the accelerator (21) the detector subsystem (11) placed on a flat mannequin (12) perpendicular to the radiation beam in the different needed conditions, defined by the different institutions' recommendations to characterize the beam.

b. Calibration of the reading of the detector subsystem (11) placed on the flat mannequin (12) (FIG. 11), comparing the obtained value with the value from another detection medium used as a standard reference (for example, an ionizing chamber), including in such calibration, if needed, the correction of the dark current effect in the detector subsystem.

c. Automated obtaining of the detector subsystem (11) dosimetric response placed inside the flat mannequin (FIG. 12), perpendicular to the radiation beam: it allows getting the parameters that characterize the accelerator beam, as non-limiting example: depth-output curve (FIG. 2 or 111), dose profiles (112) and output factor (FIG. 4 or 113) for different field sizes.

d. Automated dose calibration in the axial plane of the detection medium placed inside a cylindrical mannequin (14) (FIG. 13), including therefore a second dose calibration, according to the angle of incidence (FIGS. 5, 6 and 7), taking as reference the data from a planning system in the same conditions, including, if needed, the correction of the effect caused by the dark current.

e. 3D reconstruction (114) of the radiotherapy treatment (FIG. 8) applied on the detector subsystem (11) based on the measurements taken with the detector subsystem in the axial plane using the radon transform. The 3D reconstruction is obtained using 2D reconstructed images.

f. Verification and automated visualization of the dose map reconstructed from the measurements taken with the detector subsystem (11), with the dose map obtained with a TPS and the response obtained from the accelerator output logs for the treatment, using different parameters, being non-limiting examples the calculation of the gamma index (FIG. 9 or 115) and DVH histograms (116) that relate the dose received by each organ to a volume.

The method (1) to verify radiotherapy treatments relies on the use of a system. Such system has a detector subsystem (11) formed by a set of semiconductor segment strip or pixel detectors, preferably silicon ones, set in parallel planes, which can be placed on a bunker (31), as shown in FIGS. 10-13, positioned in a flat mannequin (12) that allows containing the detector subsystem (11) or a cylindrical or anthropomorphic mannequin (14) that allows containing the detector subsystem (11) in a parallel plane to the radiation beam. The detection mediums (11) allow obtaining a spatial resolution better than 2 mm.

The system also has readable mediums (13) for the output of the detector subsystem, which are placed on a bunker (31). The readable mediums (13) of the detector subsystem (11) are based on a digitizer whose relation between sampling frequency and number of bits allows obtaining a measurement uncertainty better than 2%.

At the same time, the system has some mediums outside the bunker to control the readable mediums and the rotation of the cylindrical mannequin subsystem, with an angle sensor subsystem (15) that allows coordinating not only the angular position of the cylindrical mannequin (14) in relation to the accelerator's head but also the speed of the movement and a communication system (1) between the accelerator (21) and the readable mediums, placed next to the control system of the system (32) outside the bunker. The mediums to control the readable mediums (13) also allow visualizing the captured data and applying the method that integrates the characterization of the radiation beam of an accelerator and the verification of a 3D radiotherapy treatment; based not only on the measurements obtained in the same output plane from such radiation beam with the detection mediums, but also on the analysis and information processing included in the accelerator logs.

The system also has a communication subsystem (3) between the readable mediums placed on the bunker (31) and the control mediums of the readable mediums (13), preferably Ethernet.

Figure 1:
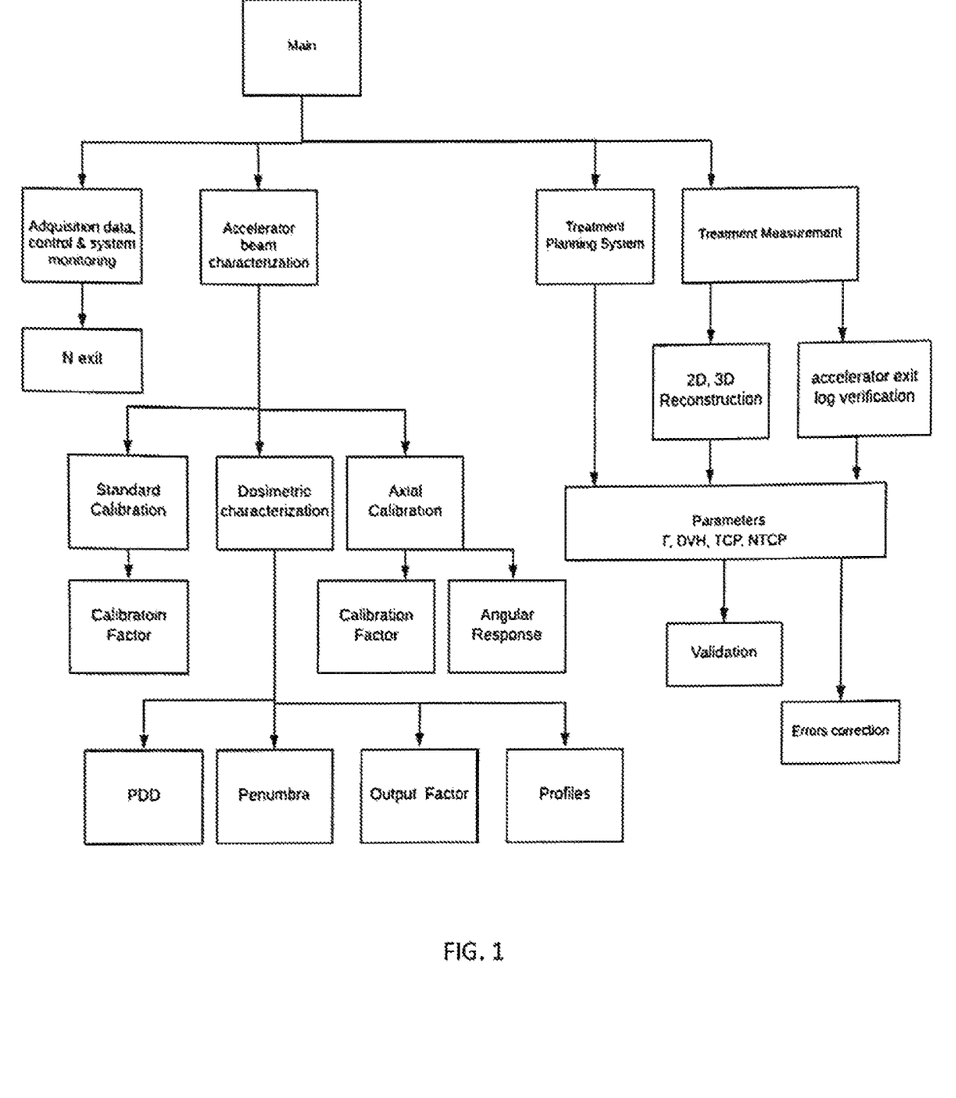
FIG. 1 shows the general diagram of an application architecture implementing the methodology of the invention.
Figure 3:
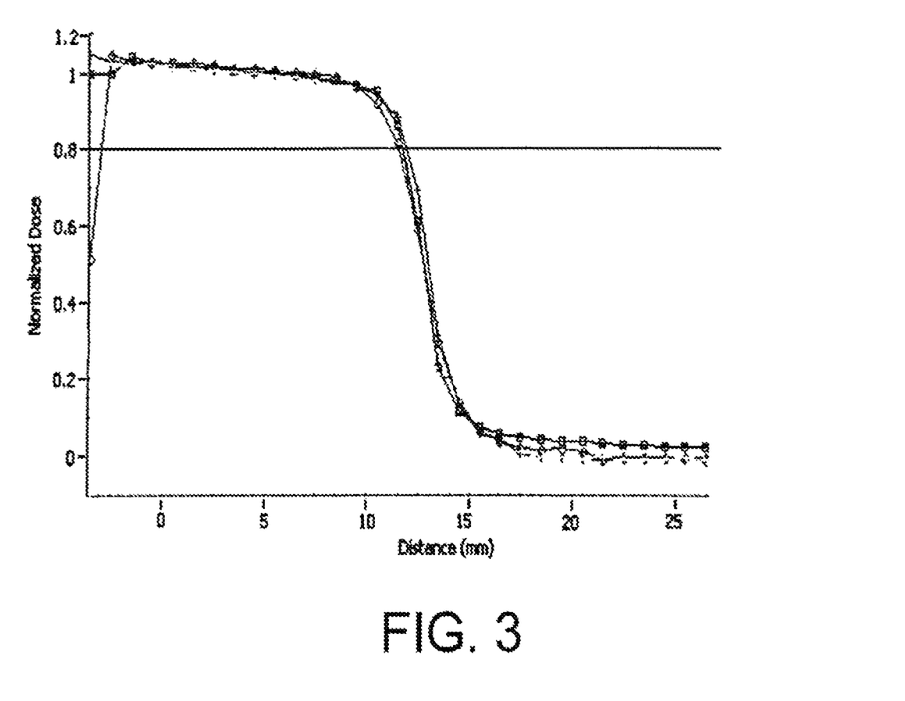
FIG. 3 shows how the calculation of the penumbra obtained with a segmented silicon strip detector applying the methodology is visualized.

More concretely and according to FIG. 1, the methodology of the invention starts from an initial state allowing the user to select the beginning of a methodology application among the three possible ones: data acquisition, control and monitoring of the system; characterization of the accelerator beam; and verification of the treatment. The characterization of the accelerator beam allows selecting the beginning of the procedure to calibrate in standard conditions, a dosimetric characterization and an axial characterization of a detection medium. From the standard calibration we get the calibration factor, whereas from the axial calibration we get a calibration factor and the angular response, getting in line a dosimetric characterization from which the PDD; the penumbra (FIG. 3 or 144) and the output factor; and the profiles are obtained. The verification, prior measurement of the treatment in the axial system, allows access to the 3D reconstruction based on such measurements, to the TPS calculation, and to the results of the accelerator logs after supplying the measured treatment, allowing access to the parameters, of validation, validating or correcting mistakes, if the parameters do not meet the established criteria as being safe for the treatment.

Regarding the procedure to verify radiotherapy treatments, the method and system allow collecting automated data for every angular position of the detection medium and for the information included in the accelerator logs, in order to later visualize the reconstruction of the dose map and the parameters calculation that allow its verification, as non-limiting example, the gamma index.

The method gives the user the possibility to select the cGy/UM relation according to the accelerator energy. The method allows obtaining the dose calibration factor under standard conditions and reference conditions; the tables relating to the available dose profile; the calculation of the percentage depth-dose inside the mediums for the user; visualizing the calculation of the penumbra obtained with the semiconductor detector medium, applying the methodology and the output factor calculation.

Figure 7:
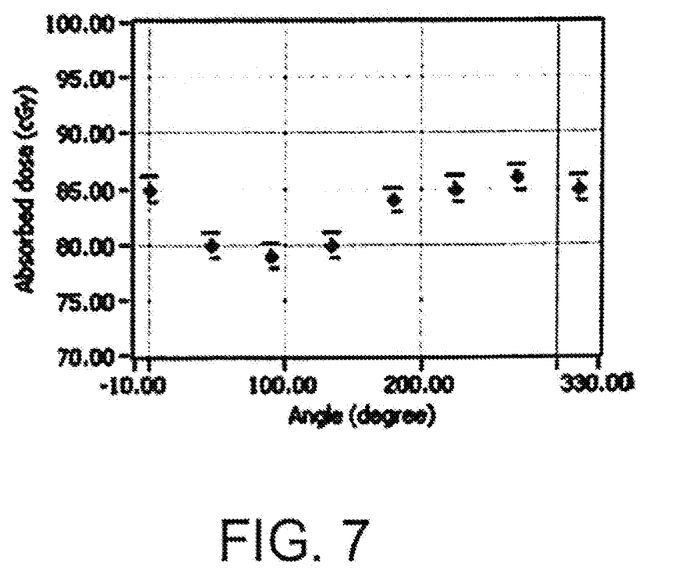
FIG. 7 illustrates the results once the procedure for the final calibration in the axial plane is applied.

The method and system allow the user to visualize the axial characterization with the detector subsystem. The user may monitor the comparison between responses to the different equal incident angles (FIG. 6), and also visualize the data of the planner and the data obtained for the detector (FIG. 5), and the calibration factor for each angle as well as seeing the final calibration (FIG. 7).

Figure 9:
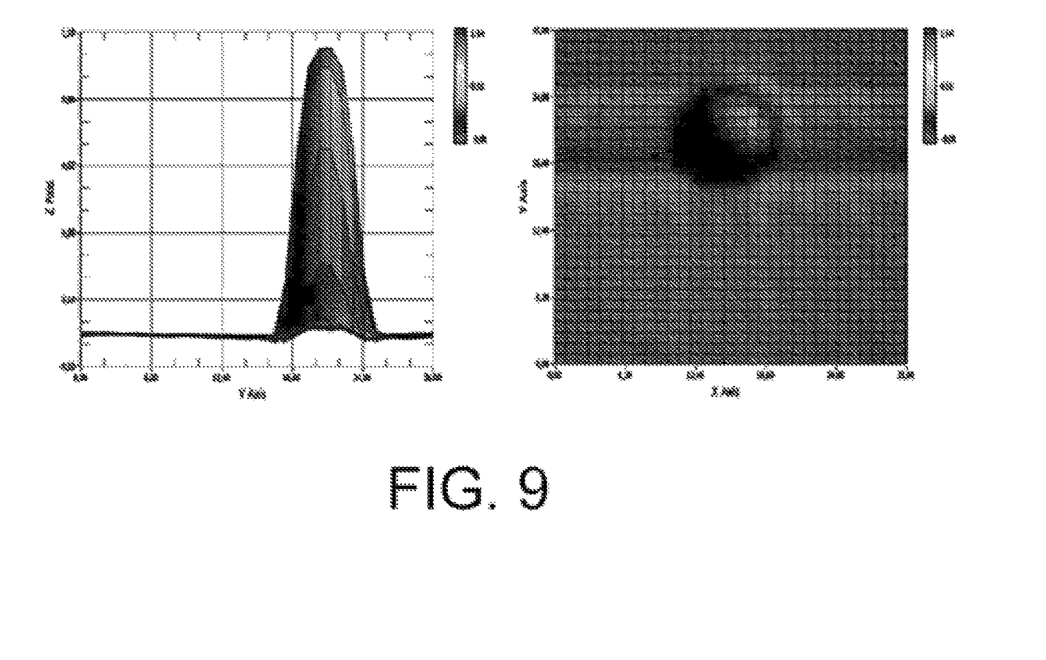
FIG. 9 shows a map with the result of the gamma factor calculation, the reference file may be selected, as this is usually obtained by the planner, and the reconstructed dose map file to check the validity of the outcome.
Figure 10:
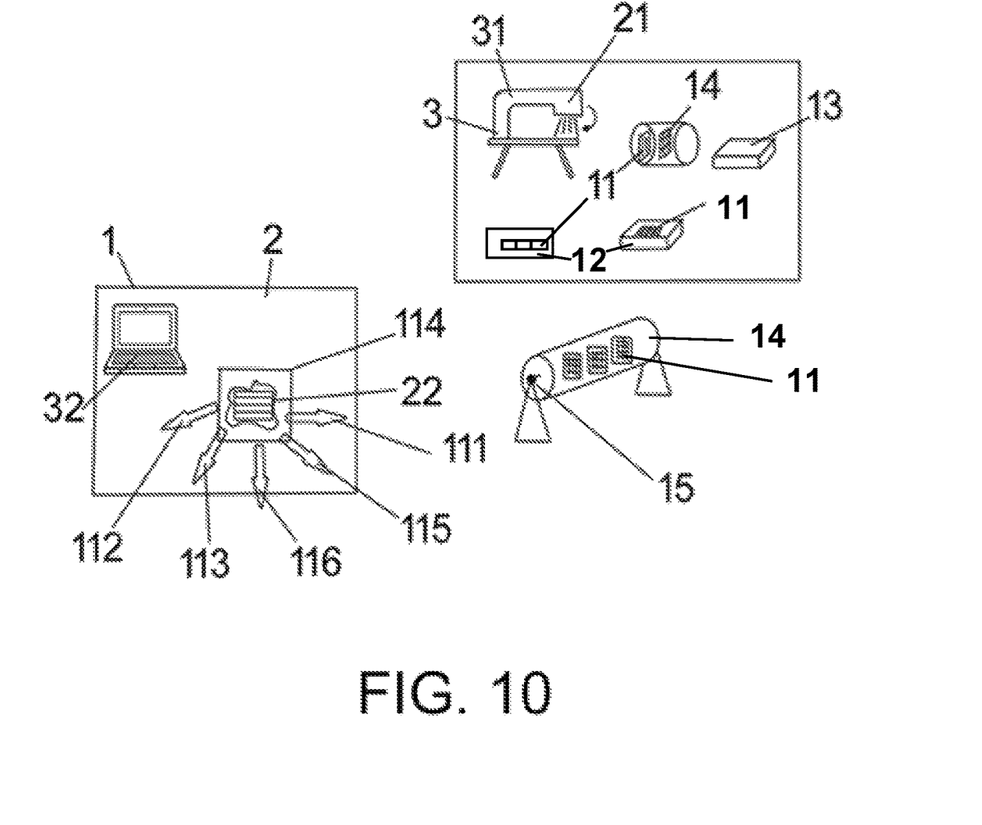
FIG. 10 shows a schematic diagram of the installation or system planned for the implementation of the previously described method.
Figure 11:
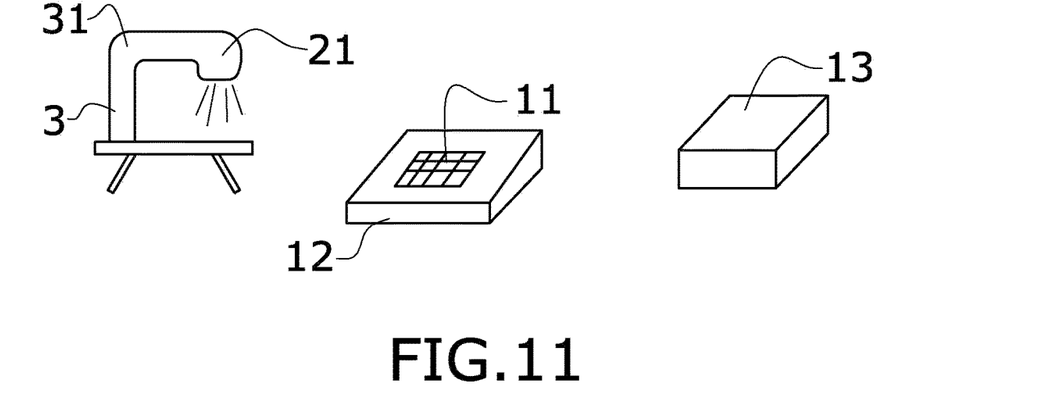
FIG. 11 shows a schematic diagram of the installation or system planned for the implementation of the previously described method with a detector subsystem placed on a flat mannequin.
Figure 12:
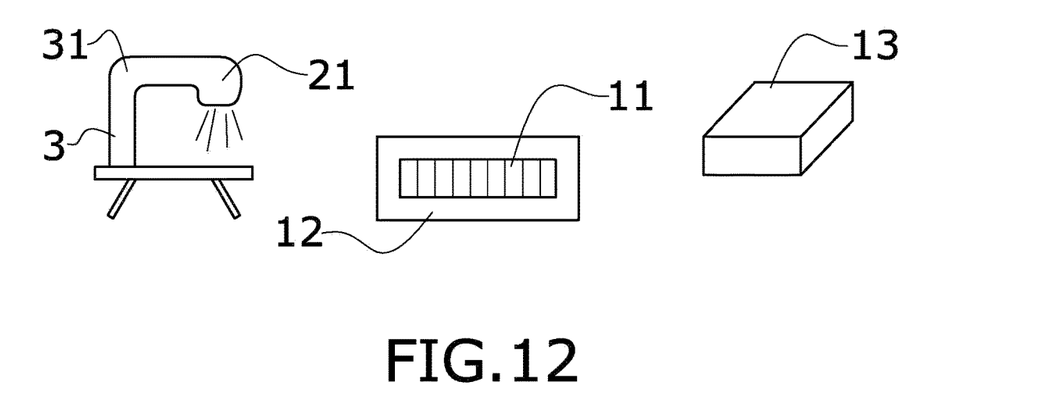
FIG. 12 shows a schematic diagram of the installation or system planned for the implementation of the previously described method with a detector subsystem placed inside a flat mannequin.
Figure 13:
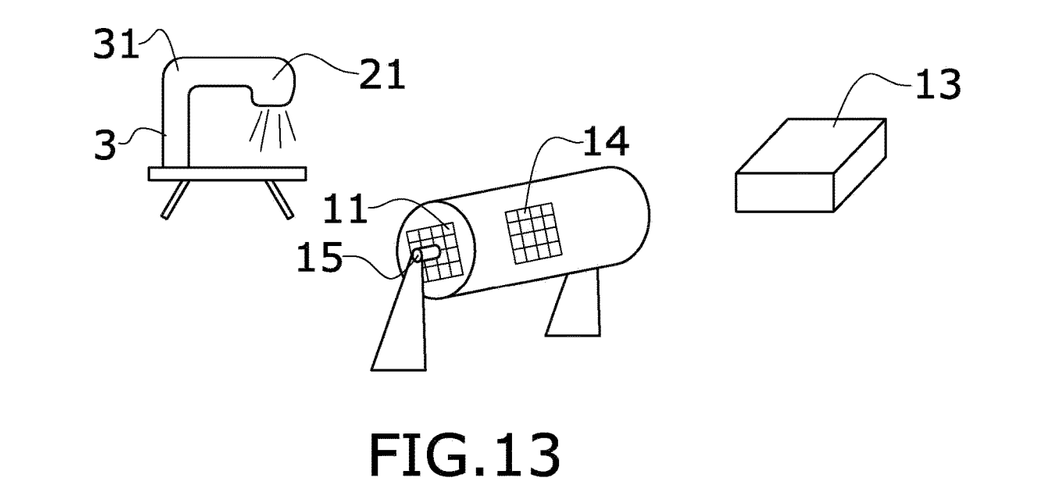
FIG. 13 shows a schematic diagram of the installation or system planned for the implementation of the previously described method with a detector subsystem placed on inside a cylindrical mannequin.

FIG. 9 shows a non-limiting example of the algorithm application for the dose map reconstruction for a 32-strip detection medium, for a circular dose distribution (whose circle is not in the middle) with radius 3a (where a is the strip width). On the left it is shown the Y axis projection or the dose profile. On the right it is shown the dose distribution in the X, Y plane.

Finally, FIGS. 10-13 show a map with the result of the 2D gamma factor calculation. The reference file may be selected, as this is usually obtained by the planner, and the reconstructed dose map file to check the validity of the outcome.

The invention claimed is:

1. A method for a dosimetric calibration and verification of complex radiotherapy treatments included in a setting, to characterize a radiation beam of an accelerator and to verify a radiotherapy treatment, comprising:

control and monitoring of reading systems after irradiating with the radiation beam of the accelerator by a first detector placed on a flat mannequin;

calibration of a reading of the first detector by comparing an obtained value with a value from another detection medium used as a standard reference, including a correction of a dark current effect in the first detector;

automated obtainment of a dosimetric response of a second detector placed inside the flat mannequin, thereby attaining parameters to characterize the radiation beam of the accelerator;

automated calibration of a third detector in an axial plane placed inside a cylindrical or anthropomorphic mannequin, including the correction of the dark current as needed;

3D reconstruction of an applied radiotherapy treatment based on measurements taken with the first, second and third detectors in the axial plane;

verification and automated visualization of a dose map reconstructed from the measurements taken with the first, second and third detectors with the dose map obtained with a planning system, through a calculation of a gamma index and DVH histograms that relate a dose received by each organ to a volume; and automated verification of a response in accelerator output logs for the applied radiotherapy treatment.

2. The method of claim 1, wherein at least one of the following parameters are obtained to characterize the radiation beam of the accelerator: depth-output curve, dose profiles and output factor for different field sizes and energies.

3. The method of claim 1, further comprising evaluation of a dose distribution provided by the accelerator with a direct measurement at an accelerator output and with analysis and process of information included in the accelerator output logs.

4. The method of claim 3, wherein digitized information from the direct measurement at the accelerator output, information obtained from computer files and information from the planning system are evaluated.

5. A system for implementing the method of claim 1, comprising:
the detector subsystem formed by a set of semiconductor segmented strip detectors placed on a bunker;
readable mediums of an output of the detector subsystem placed on the bunker;
control mediums placed next to a control system outside the bunker, the control mediums configured to control the readable mediums;
a first communication system between the readable mediums placed on the bunker and the control mediums;
the flat mannequin configured to contain the detector subsystem;
the cylindrical or anthropomorphic mannequin configured to contain the detector subsystem in a plane parallel to the radiation beam of the accelerator;
an angle sensor configured to meet an angular position of the cylindrical or anthropomorphic mannequin in relation to an accelerator head; and
a second communication system between the accelerator and the readable mediums.

6. The system of claim 5, wherein the semiconductor segmented strip detectors are segmented silicon strip detectors.

7. The system of the claim 5, wherein the readable mediums of the detector subsystem are based on a digitizer, having a relation between a sampling frequency and a number of bits, that allow obtaining a measurement uncertainty better than 2% and a dose resolution better than a hundredth.

8. The system of claim 5, wherein the detector subsystem presents a spatial resolution fewer than 2 mm.

9. The system of claim 5, wherein the control mediums comprise mediums to visualise captured data and to integrate a characterization of the radiation beam of the accelerator and the verification of a 3D radiotherapy treatment based on measurements obtained in a same output plane of the radiation beam with the detector subsystem.

10. The system of claim 5, wherein the communication system is Ethernet.

11. The system of claim 5, further comprising communication mediums and data storage mediums that communicate among and connect to different elements of the system.

* * * * *